US010463504B2

(12) United States Patent
Vestgaarden

(10) Patent No.: US 10,463,504 B2
(45) Date of Patent: Nov. 5, 2019

(54) INTERCONNECTED LOCKING PLATES FOR ADJACENT SPINAL VERTEBRAL BODIES

(71) Applicant: VGI Medical, LLC, Largo, FL (US)

(72) Inventor: Tov Inge Vestgaarden, Madeira Beach, FL (US)

(73) Assignee: VGI Medical, LLC, Largo, FL (US)

( * ) Notice: Subject to any disclaimer, the term of this patent is extended or adjusted under 35 U.S.C. 154(b) by 0 days.

(21) Appl. No.: 15/960,118

(22) Filed: Apr. 23, 2018

(65) Prior Publication Data
US 2018/0243105 A1 Aug. 30, 2018

Related U.S. Application Data

(63) Continuation of application No. 14/534,884, filed on Nov. 6, 2014, now abandoned, which is a (Continued)

(51) Int. Cl.
*A61F 2/44* (2006.01)
*A61F 2/30* (2006.01)

(52) U.S. Cl.
CPC .... *A61F 2/447* (2013.01); *A61F 2002/30364* (2013.01); *A61F 2002/30471* (2013.01); (Continued)

(58) Field of Classification Search
CPC .......... A61F 2/44; A61F 2/4405; A61F 2/442; A61F 2/4425; A61F 2/4455; A61F 2/446; A61F 2/4465; A61F 2/447; A61F 2/4611; A61F 2002/443; A61F 2002/4435; A61F 2002/448; A61F 2220/0025; A61F 2220/0033; A61B 2017/7073
See application file for complete search history.

(56) References Cited

U.S. PATENT DOCUMENTS 5,683,394 A 11/1997 Rinner
7,621,938 B2 11/2009 Molz, IV
(Continued)

OTHER PUBLICATIONS

Extended European Search Report for European Application No. 12833016 dated May 28, 2015; Applicant: Vestgaarden, Tov Inge.
(Continued)

*Primary Examiner* — Eric S Gibson
(74) *Attorney, Agent, or Firm* — Pandiscio & Pandiscio

(57) ABSTRACT

A device for insertion into a gap between adjacent, spaced apart bony elements includes an adjustable length interconnecting member having a distal and a proximal retention plate secured to opposite ends of the interconnecting member. The distal retention plate has a non-rotated position and a plurality of rotated positions. The non-rotated position aligns the distal retention plate with the gap prior to and during insertion of the distal retention plate into the gap. The distal retention plate is rotated after it has exited the gap on a distal side of the gap to prevent its return into the gap. The proximal retention plate is misaligned with the gap so that it cannot enter into the gap. The rotated distal retention plate cooperates with the proximal retention plate to hold bony elements such as adjacent vertebral bodies in a stable relationship to one another when the interconnecting member is shortened.

13 Claims, 6 Drawing Sheets

Related U.S. Application Data continuation-in-part of application No. 13/238,524, filed on Sep. 21, 2011.

(52) U.S. Cl.
CPC .............. *A61F 2002/30472* (2013.01); *A61F 2002/30484* (2013.01); *A61F 2002/30538* (2013.01); *A61F 2002/30556* (2013.01); *A61F 2002/30576* (2013.01); *A61F 2002/30578* (2013.01); *A61F 2002/30579* (2013.01); *A61F 2002/30616* (2013.01); *A61F 2002/30626* (2013.01); *A61F 2002/30777* (2013.01); *A61F 2002/30779* (2013.01); *A61F 2002/30785* (2013.01); *A61F 2002/30836* (2013.01); *A61F 2002/30841* (2013.01); *A61F 2002/30843* (2013.01); *A61F 2002/30904* (2013.01); *A61F 2002/4475* (2013.01); *A61F 2250/0007* (2013.01); *A61F 2250/0065* (2013.01); *A61F 2310/00017* (2013.01); *A61F 2310/00023* (2013.01); *A61F 2310/00179* (2013.01)

(56) References Cited

U.S. PATENT DOCUMENTS

| | | |
|---|---|---|
| 2002/0161441 A1 | 10/2002 | Lang et al. |
| 2005/0159813 A1 | 7/2005 | Molz, IV |
| 2007/0010889 A1 | 1/2007 | Francis |
| 2008/0114456 A1 | 5/2008 | Dewey et al. |
| 2008/0132949 A1 | 6/2008 | Aferzon et al. |
| 2008/0161926 A1 | 7/2008 | Melkent et al. |
| 2008/0183211 A1 | 7/2008 | Lamborne et al. |
| 2009/0187247 A1 | 7/2009 | Metcalf, Jr. et al. |
| 2009/0234389 A1 | 9/2009 | Chuang et al. |
| 2010/0241166 A1 | 9/2010 | Dwyer et al. |
| 2010/0318127 A1 | 12/2010 | Phan et al. |
| 2011/0166600 A1 | 7/2011 | Lamborne et al. |
| 2012/0004729 A1* | 1/2012 | Zipnick .......... A61B 17/320016 623/17.16 |
| 2012/0221051 A1* | 8/2012 | Robinson ........... A61B 17/7068 606/249 |
| 2012/0239089 A1 | 9/2012 | Druma et al. |
| 2014/0324103 A1 | 10/2014 | Levieux et al. |
| 2016/0367379 A1* | 12/2016 | Refai .................... A61F 2/447 |

OTHER PUBLICATIONS

International Search Report and Written Opinion dated Feb. 26, 2013 for corresponding International (PCT) Patent Application No. PCT/US2012/056304 with an international filing date of Sep. 20, 2012.

International Preliminary Report on Patentability dated Apr. 3, 2014 for corresponding international (PCT) Patent Application No. PCT/US2012/056304 with an international filing date of Sep. 20, 2012.

* cited by examiner

INTERCONNECTED LOCKING PLATES FOR ADJACENT SPINAL VERTEBRAL BODIES

CROSS-REFERENCE TO RELATED APPLICATIONS

This patent application is a continuation of pending prior U.S. patent application Ser. No. 14/534,884, filed Nov. 6, 2014 by VG Innovations, LLC for INTERCONNECTED LOCKING PLATES FOR ADJACENT SPINAL VERTEBRAL BODIES, which in turn is a continuation-in-part of pending prior U.S. patent application Ser. No. 13/238,524, filed Sep. 21, 2011 by Tov Inge Vestgaarden for METHOD AND APPARATUS FOR SPINAL INTERBODY FUSION INCLUDING FIXATION OR LOCKING PLATE. The two (2) above-identified patent applications are hereby incorporated herein by reference.

BACKGROUND OF THE INVENTION

1. Field of the Invention

This invention relates to surgical methods and apparatus in general, and more particularly to surgical methods and apparatus for fusing spinal vertebral bodies.

2. Brief Description of the Related Art

In disc herniation, a spinal disc bulges from between two vertebral bodies and impinges on adjacent nerves, causing pain. In some cases, non-operative procedures such as bed rest, medication, lifestyle modifications, exercise, physical therapy, chiropractic care and steroid injections may suffice. However, in other cases, surgical intervention may be necessary. In cases where surgical intervention is prescribed, spinal vertebral body fusion may be desirable, i.e., the spine may have deteriorated so much that adjacent vertebral bodies must be fused together.

Spinal fixation is the current standard of care for surgically treating disc herniation in patients who have chronic pain and who have, or are likely to develop, associated spinal instability. Spinal fixation procedures are intended to relieve impingement on nerves by removing the portion of the disc or bone, or both, responsible for compressing the neural structures and destabilizing the spine.

The prior art teaches that excised disc or bone must be replaced with one or more intervertebral implants, or spacers, placed between adjacent vertebral bodies. These implants stabilize the adjacent vertebral bodies relative to one another so that the two vertebral bodies can fuse together.

The prior art considered as a whole at the time the present invention was made does not include any discussion concerning whether or not spinal fixation can be accomplished in the absence of a spinal fusion implant. It necessarily follows that it was not obvious to those of ordinary skill in the art at the time the present invention was made that spinal fixation could be accomplished in the absence of spinal fusion implants.

SUMMARY OF THE INVENTION

The long-standing but heretofore unfulfilled need for an improved spinal fusion implant is now met by a new, useful, and non-obvious invention.

The novel structure does not include a spinal fusion implant having a main body having a predetermined length, width, and thickness as disclosed in all prior art literature relating to spinal fusion implants.

However, the novel structure stops motion between adjacent vertebral bodies, thereby allowing fusion to occur. Conventional fusion accelerants, such as bone, are added to the empty space conventionally occupied by a spinal fusion implant main body in order to promote fusion.

The novel main body-less spinal fusion implant is inserted into a gap between adjacent, spaced apart vertebral bodies in a spinal joint, said gap created by surgical removal of a disc.

The novel spinal fusion implant includes an elongate interconnecting member that may have a fixed length or an adjustable length, a distal retention plate rotatably secured to a distal end of the interconnecting member, and a proximal retention plate secured to a proximal end of the interconnecting member.

The distal retention plate has an unrotated position of repose and an infinite plurality of rotated positions relative to said position of repose. Similarly, the proximal retention plate may have an unrotated position of repose and an infinite plurality of rotated positions relative to the position of repose.

When the distal and proximal retention plates are in their respective positions of repose, they are rotationally aligned with one another.

The proximal retention plate may be fixedly secured into its operable position so that it does not rotate relative to the interconnecting member but can be rotated conjointly with the interconnecting member.

The distal retention plate is in its position of repose when it is inserted into the surgically-created gap between adjacent vertebral bodies and is in a rotated position after the distal retention plate has cleared the distal surface of the spinal vertebral bodies, i.e., when the distal retention plate has passed through and is not positioned in said gap.

The distal retention plate when in the second position after said insertion abuts the superior and inferior vertebral bodies on the distal side of the spine and therefore prevents distal-to-proximal travel of the distal retention plate and thus prevents retraction of the interconnecting member from the gap and cooperates with the rotated proximal retention plate to hold adjacent vertebral bodies in a stable relationship to one another.

After the distal retention plate has cleared the distal spinal vertebral bodies and is rotated to prevent its re-entry into the gap, the interconnecting member is shortened to cause the proximal and distal retention plates to converge toward one another, thereby tightly sandwiching the adjacent vertebral bodies between them and holding said adjacent vertebral bodies against movement.

The rotation of the distal retention plate is preferably a ninety degree (90°) rotation relative to its position of repose, but the distal retention plate can still perform its function when rotated less than ninety degrees (90°) and such reduced angles of rotation are within the scope of this invention.

Both retention plates may have a roughened inboard surface to enhance their respective grips on their respective vertebral bodies.

Both retention plates may also have at least one protrusion formed on an inboard surface thereof to enhance their respective grips on their respective vertebral bodies.

The maximum length of the adjustable length interconnecting member is sufficient to span the proximal-to-distal extent of the gap and to allow the proximal and distal retention plates to be positioned outside the gap. The minimum length of the adjustable length interconnecting member is sufficient to enable the distal and proximal retention plates to tightly grip the adjacent vertebral bodies in sandwiched relation between them.

The proximal retention plate may be in its unrotated position of repose, rotationally aligned with the distal retention plate during distal retention plate insertion, or it may be rotated into its deployed configuration prior to insertion of the distal retention plate because the proximal retention plate does not enter into the gap.

The length of the interconnecting member is fixed or adjustable by any suitable mechanical means. The retention plates converge toward one another when the length of the interconnecting member is shortened, thereby holding the adjacent vertebral bodies in a stable relationship to one another as aforesaid.

The suitable mechanical means may include providing the interconnecting member in telescoping form.

As in the incorporated patent, the novel device does not require incisions on both sides of the spine, thereby obtaining an important object of the invention, i.e., providing a spinal fusion device that does not require incisions on both sides of a spine.

Another important object is to provide a spinal fusion device having no main body as in all prior art spinal fusion devices.

A more specific object is to provide a spinal fusion device that is inserted from a proximal side of a spine and which has a distal retention plate mounted on the distal end of an adjustable length interlocking member where the distal retention plate is aligned with a gap formed between adjacent vertebral bodies and inserted through said gap until the distal retention plate clears the distal edge of the adjacent vertebral bodies.

A closely related object is to provide a device that is inserted from a proximal side of a spine and which has a proximal retention plate mounted on the proximal end of an adjustable length interlocking member where the proximal retention plate may be aligned with the gap formed between adjacent vertebral bodies but which is not inserted into said gap.

Another closely related object is to provide a tool where distal and proximal retention plates are respectively mounted to distal and proximal ends of an adjustable length interconnecting member and where the distal retention plate is in a non-rotated position during insertion and in a rotated, deployed configuration after insertion.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

A spine includes a plurality of vertebral bodies separated by discs. A spine may deteriorate so much that adjacent vertebral bodies must be fused together. The novel spinal fusion implant is disposed between contiguous vertebral bodies to immobilize the affected segment of the spine and facilitate fusion between said adjacent vertebral bodies.

Prior art spinal fusion devices include a main body that substantially fills the gap between adjacent vertebral bodies. However, it has been discovered by the present inventor that fusion can occur in the absence of a main body. With a lower mass in the disc space, there is an increased chance, but no guarantee, of subsidence. Any structure with bleeding bone and micro motion will grow together. In this case the bleeding bone will grow to the distal and proximal plates where they attach to the vertebral bodies or directly between adjacent vertical bodies. If a surgeon adds autograft, allograft, or biologics to the disc space, this will be the traditional method of fusion.

The spine is prepared by removing some or all of the disc that resides in the space where the novel spinal fusion implant is to be inserted. The disc space is prepared with a rongeur or other surgical instrument, not depicted.

The novel structure effectively stabilizes the joint but permits the occurrence of "micro-motion" between the opposing vertebral bodies, which is important for successful bone fusion.

Figure 1:
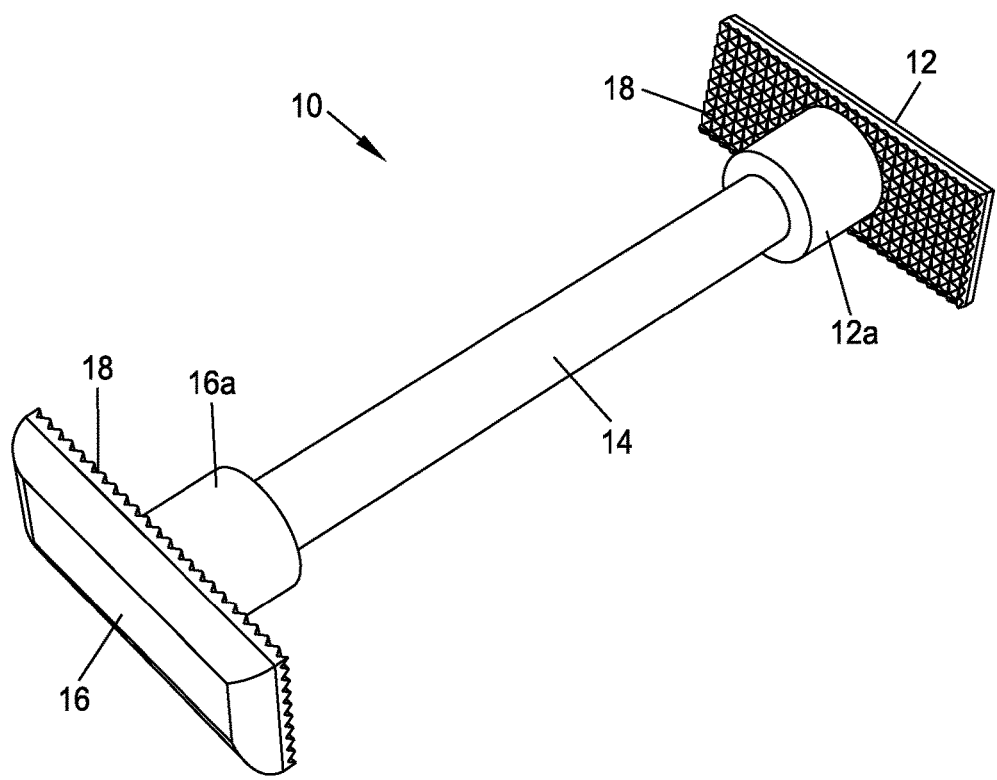
FIG. 1 is a perspective view of a first embodiment of the invention.
Figure 2:
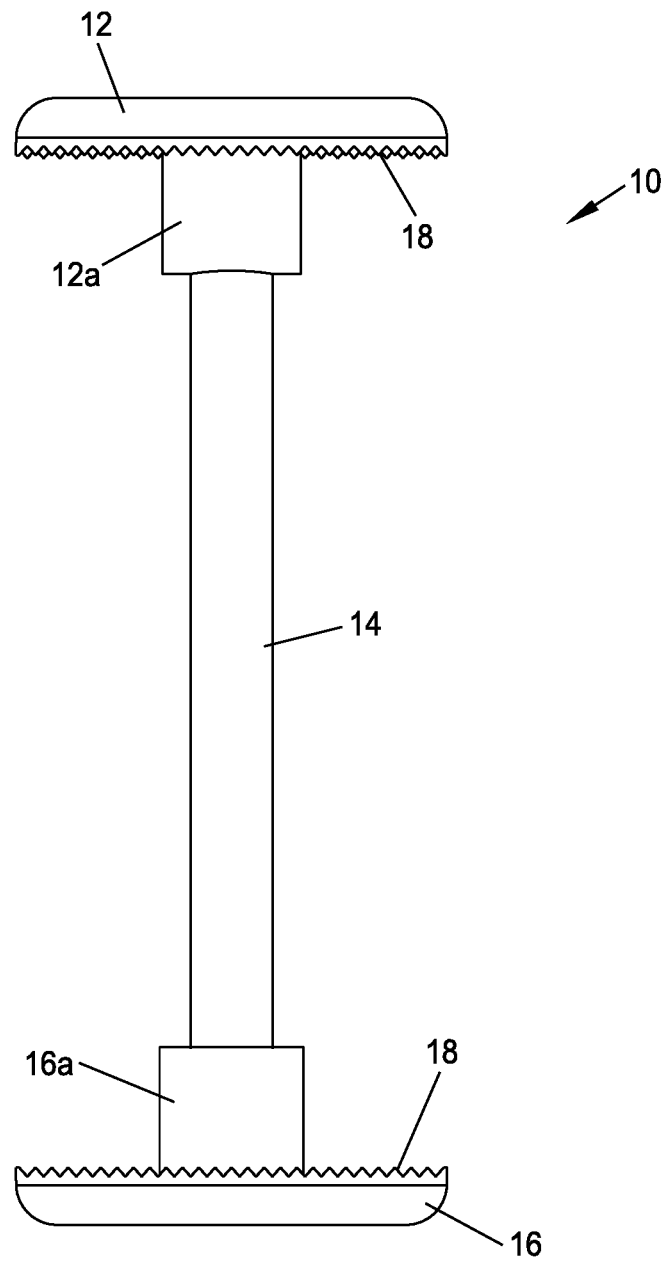
FIG. 2 is a top plan view thereof.
Figure 3:
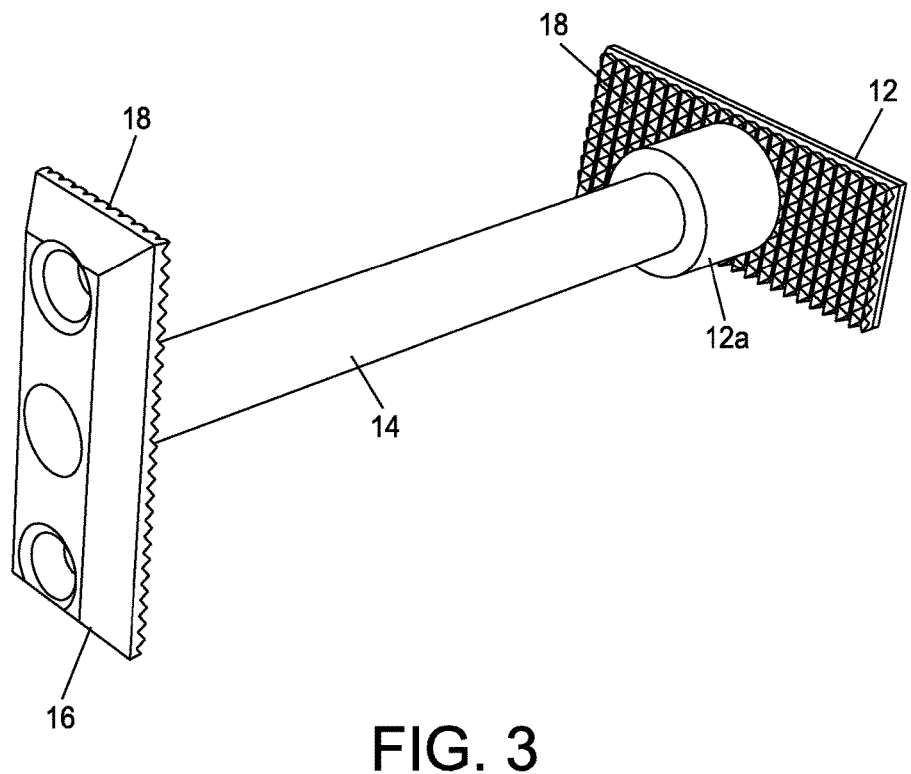
FIG. 3 is a perspective view of a second embodiment.

Referring now to FIGS. 1-3, novel tool 10 includes distal retention plate 12 which is attached to the distal end of elongate interconnecting member 14. Proximal retention plate 16 is attached to the proximal end of said elongate interconnecting member 14. Proximal retention plate 16 may be mounted for relative rotation with respect to interconnecting member 14 or it may be fixedly secured thereto or integrally formed therewith for conjoint rotation therewith.

Boss 12a may be formed integrally with distal retention plate 12 and boss 16a may be formed integrally with proximal retention plate 16, said bosses receiving the opposite ends of interconnecting member 14 to enhance the structural integrity of the novel structure. There is no relative rotation and no longitudinal displacement between the bosses and said opposite ends.

In the embodiments of FIGS. 1-3, rotation of proximal retention plate 16 by a surgeon effects conjoint rotation of distal retention plate 12. Said plates may be in rotational alignment with one another in a first embodiment as depicted in FIGS. 1 and 2, or they may be rotated ninety degrees (90°) with respect to one another in a second embodiment as depicted in FIG. 3. Other angular orientations between the retention plates are within the scope of this invention.

The first embodiment of this invention as illustrated is a non-telescoping embodiment. All other embodiments have telescopically interconnected parts. The first embodiment could also be modified so that the distal and proximal plates could be telescopically interconnected to one another.

As shown in FIG. 3, proximal retention plate 16 has at least two (2) openings that receive screws so that plate 16 may be secured to the vertebral bodies.

Each retention plate preferably has a roughened inboard surface as at 18. The inboard surface is the surface that abuts the patient's body. At least one protuberance may also be formed in the respective inboard surfaces of distal and proximal retention plates 12 and 16, respectively. Such protuberances would perform the same gripping function as the aforesaid roughened surfaces. The use of only one (1) protrusion is within the scope of this invention and is considered the equivalent of a roughened surface.

Figure 4:
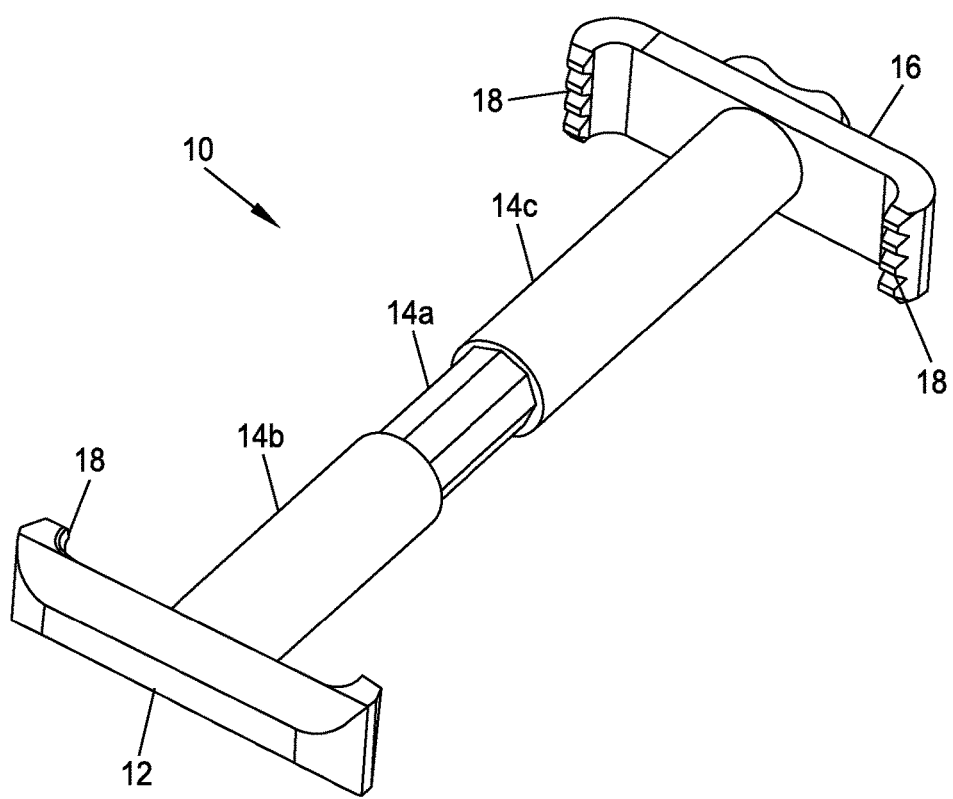
FIG. 4 is a perspective view of a third embodiment.

FIG. 4 depicts a third embodiment. Retention plates 12 and 16 in this embodiment have a square bracket ([) shape with rounded corners and the retention plates 12, 16 contact the patient's body only at the inboard-projecting opposite ends of such retention plates. The body-contacting opposite ends have roughened surfaces 18 similar to the roughened surfaces of the first embodiment.

Elongate interconnecting member 14 in this embodiment has three parts, i.e., elongate base 14a having an octagonal transverse cross-section, distal part or sleeve 14b which is formed integrally with or fixedly secured to distal retention plate 12 for conjoint rotation therewith, and proximal part or sleeve 14c which is formed integrally with or fixedly secured to proximal retention plate 16 for conjoint rotation therewith.

Parts 14b and 14c are provided with octagonal lumens that telescopically mate with elongate base 14a. A surgeon may insert distal retention plate 12 through the disc space until said distal retention plate clears the vertebrae while holding proximal retention plate 16 in the position depicted in FIG. 4. Rotation of proximal retention plate 16 then effects conjoint rotation of distal retention plate 12 just as in the first three embodiments. The difference is that said retention plates of this second embodiment are telescopically interconnected so that tool 10 can be used with patients of varying sizes. Thus it is understood that the transverse cross-section of base 14a and the mating lumens of parts 14b and 14c could be of any non-round cross-section.

Figure 5:
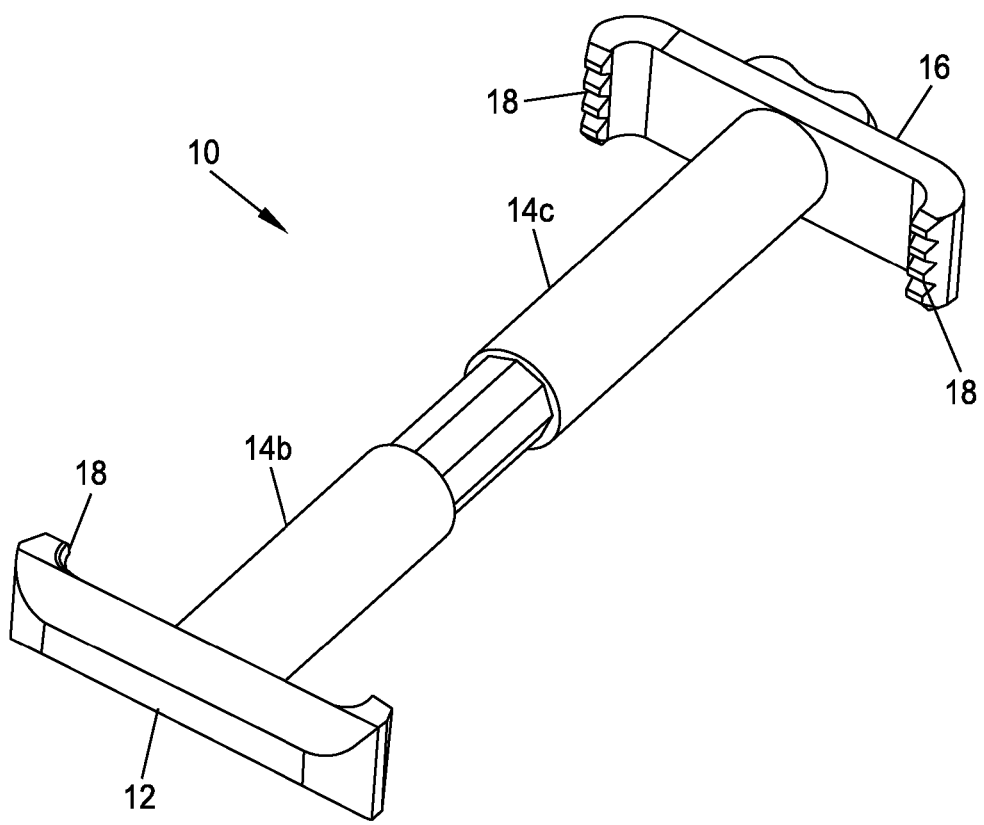
FIG. 5 is a perspective view of a fourth embodiment.

A fourth embodiment is depicted in FIG. 5. This embodiment eliminates base member 14a. Distal and proximal parts 14b, 14c telescopically engage one another. More particularly 14c has an internal lumen designed to accept the cross-sectional shape of 14b.

Figure 6:
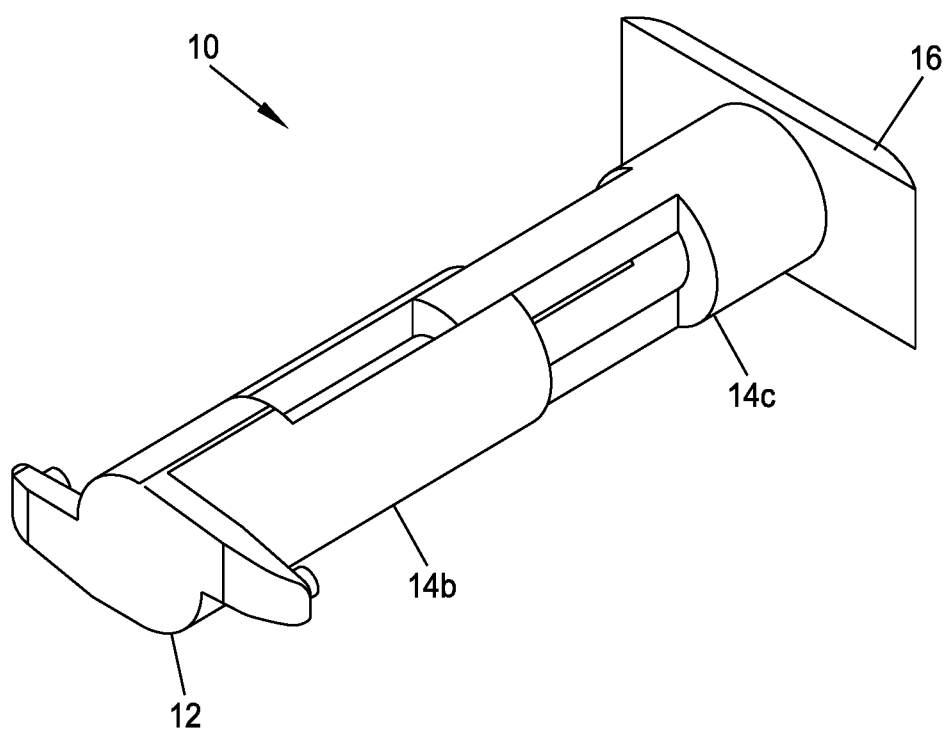
FIG. 6 is a perspective view of a fifth embodiment.

A fifth embodiment is depicted in FIG. 6. This embodiment also eliminates base member 14a. Distal and proximal parts 14b, 14c telescopically engage one another. More particularly, each part 14b, 14c has two diametrically oposed arms and two diametrically opposed slots slots so that the arms of distal part 14b slidingly engage the slots of proximal part 14c and the arms of proximal part 14c slidingly engage the slots of distal part 14b.

Distal retention plate 12 in FIG. 6 has a different structure than proximal retention plate 16 to allow plate 12 to cut through surrounding soft tissue.

Misalignment (at least some rotation) of distal retention plate 12 from its non-rotated position limits motion in a multi-directional joint. More particularly, the shape of the main body in the incorporated disclosure limits motion in flexion/extension, while distal retention plate 12 in cooperation with proximal retention plate 16 limits lateral bending. Accordingly, this main body-less embodiment does not limit motion in flexion/extension.

Thus it is understood that the spine is locked in sandwiched relation between proximal retention plate 16 on the proximal side and distal retention plate 12 on the distal side even though only one incision has been made, said incision being on said proximal side, thereby distinguishing the invention from prior art tools and methods that require two (2) incisions, i.e., incisions on both the proximal and the distal side of the spine.

Spinal fusion implant 10 is inserted into a disc space using a lateral approach. The lateral approach is preferred because it is familiar to spine surgeons, and also minimizes the possibility of damage to the spinal cord during insertion of the tool.

Although tool 10 has been disclosed in the context of fusing an intervertebral joint, it may also be used to stabilize and fuse any joint having an anatomy similar to an intervertebral joint, i.e., a pair of opposing bony surfaces defining a gap therebetween. By way of example and not limitation, the novel tool may be used in small joints as in the finger, toe, etc.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween.

What is claimed is:

1. A method for fusing two adjacent, spaced-apart vertebral bodies, the method comprising:
   providing a spinal fusion implant, the spinal fusion implant comprising:
      a distal retention plate having a long axis defining a longitudinal axis of the distal retention plate, and a short axis perpendicular to the long axis of the distal retention plate;
      a proximal retention plate having a long axis defining a longitudinal axis of the proximal retention plate, and a short axis perpendicular to the long axis of the proximal retention plate; and
      an elongated member connecting the distal retention plate to the proximal retention plate such that the longitudinal axis of the distal retention plate is parallel to the longitudinal axis of the proximal retention plate, and such that rotation of said proximal retention plate effects conjoint rotation of said distal retention plate;
   accessing the two adjacent, spaced-apart vertebral bodies through a single incision;
   removing, through the single incision, at least a portion of a disc disposed between the two adjacent, spaced-apart vertebral bodies so as to create a gap between opposing end surfaces of the two adjacent, spaced-apart vertebral bodies, wherein each vertebral body has a distal surface and a proximal surface, and further wherein the proximal surface of each vertebral body is closer to the single incision than the distal surface of each vertebral body;
   with the distal retention plate and the proximal retention plate are disposed such that the longitudinal axis of the distal retention plate and the longitudinal axis of the proximal retention plate are parallel to planes defined by the opposing end surfaces of the two adjacent, spaced-apart vertebral bodies, inserting the distal retention plate through the single incision and into the gap, and moving the spinal fusion implant distally until the distal retention plate passes through the gap and beyond the distal surfaces of the vertebral bodies;

rotating the proximal retention plate so as to effect conjoint rotation of the distal retention plate, whereby to orient the longitudinal axis of the distal retention plate and the longitudinal axis of the proximal retention plate transverse to the planes defined by the opposing end surfaces of the two adjacent, spaced-apart vertebral bodies;

moving the distal retention plate and the proximal retention plate towards one another, while the longitudinal axis of the distal retention plate and the longitudinal axis of the proximal retention plate are set transverse to planes defined by the opposing end surfaces of the two adjacent, spaced-apart vertebral bodies so as to clamp the two vertebral bodies to one another and hold the two vertebral bodies against movement relative to one another.

2. The method according to claim 1 wherein the elongated member is configured to be selectively telescoped between a longitudinally-extended configuration and a longitudinally-retracted configuration, whereby to move the distal retention plate and the proximal retention plate closer together.

3. The method according to claim 2 wherein the elongated member comprises a distal retention plate shaft member mounted to the distal retention plate and a proximal retention plate shaft member mounted to the proximal retention plate, with the distal retention plate shaft member and the proximal retention plate shaft member being telescopically connected to one another.

4. The method according to claim 3 further comprising an elongated base connecting the distal retention plate shaft member to the proximal retention plate shaft member.

5. The method according to claim 4 wherein the elongated base comprises a non-round cross section.

6. The method according to claim 5 wherein the non-round cross section is octagonal, and further wherein the distal retention plate shaft member and the proximal retention plate shaft member comprise octagonal lumens.

7. The method according to claim 1 wherein the distal retention plate and the proximal retention plate are rotationally aligned with one another during insertion of the distal retention plate into the gap.

8. The method according to claim 1 wherein the distal retention plate comprises a proximally-facing surface and the proximal retention plate comprises a distally-facing surface.

9. The method according to claim 8 wherein at least one of the proximally-facing surface of the distal retention plate and the distally-facing surface of the proximal retention plate comprises at least one projection.

10. The method according to claim 8 wherein the proximally-facing surface of the distal retention plate and the distally-facing surface of the proximal retention plate each comprise a main portion and an inboard projecting extension extending from each end of the main portion so as to form a U-shape, wherein the inboard projecting extensions of the proximally-facing surface of the distal retention plate extend toward the distally-facing surface of the proximal retention plate and the inboard projecting extensions of the distally-facing surface of the proximal retention plate extend toward the proximally-facing surface of the distal retention plate.

11. The method according to claim 10 wherein the inboard projecting extensions comprise roughened inboard surfaces.

12. The method according to claim 1 wherein the distal retention plate is rotated 90 degrees.

13. The method according to claim 1 further comprising securing the proximal retention plate to a vertebral body.

* * * * *